United States Patent
Nunes et al.

(10) Patent No.: US 7,247,273 B2
(45) Date of Patent: Jul. 24, 2007

(54) THIN LAYER CHROMATOGRAPHY RESIDUE APPLICATOR SAMPLER

(75) Inventors: Peter J. Nunes, Danville, CA (US);
Fredrick R. Kelly, Modesto, CA (US);
Jeffrey S. Haas, San Ramon, CA (US);
Brian D. Andresen, Livermore, CA (US)

(73) Assignee: The Regents of the University of California, Oakland, CA (US)

( * ) Notice: Subject to any disclaimer, the term of this patent is extended or adjusted under 35 U.S.C. 154(b) by 410 days.

(21) Appl. No.: 10/229,523

(22) Filed: Aug. 27, 2002

(65) Prior Publication Data
US 2004/0042934 A1    Mar. 4, 2004

(51) Int. Cl.
*G01N 30/00* (2006.01)

(52) U.S. Cl. .................... 422/100; 422/61; 422/99; 422/102

(58) Field of Classification Search ................ 422/50, 422/55, 56, 57, 58, 61, 68.1, 100, 99, 102, 422/104
See application file for complete search history.

(56) References Cited

U.S. PATENT DOCUMENTS 3,954,564 A * 5/1976 Mennen .................. 600/572
5,078,968 A * 1/1992 Nason ..................... 422/58
5,859,374 A * 1/1999 Mink et al. .............. 73/863
5,916,802 A * 6/1999 Andreotti ............... 435/287.7
2001/0008614 A1* 7/2001 Aronowitz ............... 422/101

* cited by examiner

*Primary Examiner*—Jill Warden
*Assistant Examiner*—Samuel P. Siefke
(74) *Attorney, Agent, or Firm*—James S. Tak; John H. Lee

(57) ABSTRACT

A thin layer chromatograph residue applicator sampler. The residue applicator sampler provides for rapid analysis of samples containing high explosives, chemical warfare, and other analyses of interest under field conditions. This satisfied the need for a field-deployable, small, hand-held, all-in-one device for efficient sampling, sample dissolution, and sample application to an analytical technique. The residue applicator sampler includes a sampling sponge that is resistant to most chemicals and is fastened via a plastic handle in a hermetically sealed tube containing a known amount of solvent. Upon use, the wetted sponge is removed from the sealed tube and used as a swiping device across an environmental sample. The sponge is then replaced in the hermetically sealed tube where the sample remains contained and dissolved in the solvent. A small pipette tip is removably contained in the hermetically sealed tube. The sponge is removed and placed into the pipette tip where a squeezing-out of the dissolved sample from the sponge into the pipette tip results in a droplet captured in a vial for later instrumental analysis, or applied directly to a thin layer chromatography plate for immediate analysis.

14 Claims, 2 Drawing Sheets

THIN LAYER CHROMATOGRAPHY RESIDUE APPLICATOR SAMPLER

The United States Government has rights in this invention pursuant to Contract No. W-7405-ENG-48 between the United States Department of Energy and the University of California for the operation of Lawrence Livermore National Laboratory.

BACKGROUND OF THE INVENTION

The present invention relates to the collection and characterization of residues, particularly to the collection of trace amounts of high explosives and chemical weapons residues for field analysis, and more particularly to a field-deployable, small, hand held, all-in-one device for efficient sampling, sample dissolution, and sample application to an analytical technique.

Over the last decade extensive efforts have been carried out for development methods for characterization of various chemicals, particularly for the characterization of high explosives, chemical weapons, and biological weapons. These activities have centered on the collection, isolation, and concentration of trace amounts of these chemical residues in air, soil, vegetation, swipe, and liquid samples. Considerable resources have been applied to developing consistent and reliable methods for field analysis of high explosives and chemical weapons related materials. For example, The Forensic Science Center (FSC) at the Lawrence Livermore National Laboratory (LLNL) has been developing new technology for the characterization of high explosives (HE) and chemical weapons (CW) in the field. These activities have centered on the collection, isolation, and concentration of trace amounts of HE, and CW residues in air, soil, vegetation, swipe and liquid samples. Considerable resources have been applied to developing consistent and reliable methods for the field analysis of HE and CW-related materials. Recently the FSC was contracted by the United States Army to take a priven laboratory technique, Thin Layer Chromatography (TLC), and bring it to field utilization to determine the chemical composition of propellants.

Solid Phase Microextraction (SPME) is a widely recognized approach for the collection of various chemical residues, and SPME fibers and syringes are commercially available. SPME requires no solvents, is sensitive to low nanogram signature species, and can be repeatedly used in the field for the characterization of complex samples. A significant attribute of SPME fibers is their exceedingly high collection efficiencies. No chemical pretreatment of solvent extraction are necessary when using SPME fibers with GC or GC-MS instrumentation. The SPME approach has been developed to point of field-deployment, as exemplified by co pending U.S. application Ser. No. 09/834,138 filed Apr. 2, 2001, entitled "Solid Phase Micro-extraction Field Kit", assigned to the same assignee, and U.S. application Ser. No. 10/126,792, filed Apr. 18, 2002, entitled "Miniature Solid Phase Micro-extraction Holder", assigned to the same assignee.

Due to the fragile nature of the SPME fiber, there is a need for a more robust approach to environmental sampling, particularly where the contamination has been deposited as a residue on a surface requiring swiping of the surface to obtain a sample. Accordingly, there still exists a need for the rapid analysis of samples containing, high explosive, chemical warfare, and other analytes of interest under field condition. Typically under field conditions, large numbers of samples are necessary from cordoned-off areas. Large sample collections of this type hinder any hope of expeditious analysis. Therefore, the development and use of a small had-held, all-in-one device for efficient sampling, sample dissolution, and sample application to an analytical technique, has been most desired by field analysts.

The present invention provides a solution to this need by utilizing a small, very robust sampling apparatus, with sample collection, sample dissolution, and sample application. The apparatus utilizing a wetted sampling sponge to collect, dissolve, and deposit a sample of interest for immediate or later instrumental analysis. The wetted sponge is retained before and after sampling in a hermetically sealed device which contains a measured amount of solvent. The device also contains a small pipette tip by which the dissolved sample can be squeezed out of the sponge into a vial for later anaylsis or directly applied to a thin layer chromatography for immediate analysis.

SUMMARY OF THE INVENTION

It is an object of the present invention to provide a residue applicator sampler.

A further object of the invention is to provide a field-deployable residue sampler.

A further object of the invention is to provide an apparatus which enable the rapid analysis of samples containing various material residues such as high explosives, chemical warfare, and other analytes of interest under field conditions.

Another object of the invention is to provide a field-deployable, a small hand-held, all-in-one device for efficient sampling, sample dissolution, and sample application to an analytical technique.

Another object of the invention is to provide a small, very robust sampling apparatus, with sample dissolution, and sample applicator.

Another object of the invention is to provide a sampling apparatus which utilizes a wetted sponge for collecting residue of interest, which wetted sponge is retained before and after use in a hermetically sealed device partially filled with a known amount of solvent, and where the device also includes a small pipette tip in which the sample laden wetted sponge is squeezed so as to capture the sample in a vial for analysis.

Other objects and advantages of the invention will become apparent from the following description and accompanying drawings. The invention basically involves a residue applicator sampler, particularly applicable for use with a thin layer chromatography, for bringing advanced analysis technologies to the field to determine the chemical composition of various materials including propellants, high explosives, chemical weapons materials, etc. The invention involves a field-deployable, small, very robust residue sampling apparatus, with sample dissolution, and sample applicator for analysis. The apparatus utilizes a wetted sponge to collect and dissolve the sample, and a small pipette tip in which the sample laden wetted sponge can be squeezed to discharge the sample therefrom for analysis. The apparatus is hermetically sealed to prevent leakage or cross-contamination. Further, since the apparatus is hermetically sealed, it can be dropped in a decontamination solution before it is handled by an analyst or before it is shipped to another location.

BRIEF DESCRIPTION OF THE DRAWINGS

The accompanying drawings, which are incorporated into and form a part of the disclosure, illustrates an embodiment of the invention and, together with the description, serve to explain the principles of the invention.

DETAILED DESCRIPTION OF THE INVENTION

The present invention involves a residue applicator sampler, particularly for use with thin layer chromatography. The invention provides a reliable tool for the field analysis of high explosives, chemical weapons, composition of propellants, and other analytes of interest under field conditions. The applicator sampler is a field-deployable small hand-held, all-in-in-one device for efficient sampling, sample dissolution, and sample application to an analytical technique. Thus, the invention is basically a small, very robust sampling apparatus, with sample dissolution, and sample applicator for analysis of the sample.

The sampling apparatus includes a sampling sponge that is resistant to most chemicals and is fastened via a plastic handle in a hermetically sealed tube on one end of the device or apparatus, that is partically filled with a known amount of a solvent so that the sponge is wetted by the solvent. The wetted sampling sponge can be kept in storage in the sealed tube or the sealed tube can be kept in a kit for long periods of time until its use.

When needed to sample an analyte of interest in the field, the wetted sponge is removed from the sealed tube and is used as a swiping device across an environmental sample or residue. The sponge, containing the sample residue, is then replaced back in the hermetically sealed tube where the sample remains contained and is dissolved by the solvent on the wetted sponge. The device is labeled and carried back to the field station for analysis. The other end of the device or apparatus contains a removable hermetically sealed tube that contains a small pipette tip. The sample laden wetted sponge is once again removed from the tube and placed into the pipette tip where a squeezing-out of the dissolved sample is focused into a very small droplet. The droplet is captured in a small vial located in the hermetically sealed tube which retains the pipette tip. The sample containing vial can be stored for later instrumental analysis, or the contained sample is applied directly to a thin layer chromatography plate for immediate analysis. Further, since the device contains hermetically sealed tubes, it can be dropped into a decontamination solution before it is handled by an analyst or before it is shipped off-site to another location.

Figure 1:
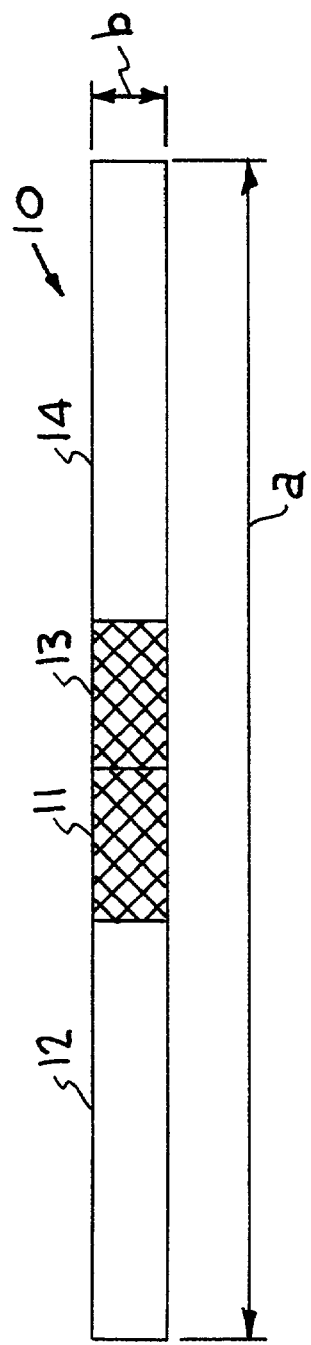
FIG. 1 is an external view of an embodiment of the residue applicator sampler of the invention.
Figure 2:
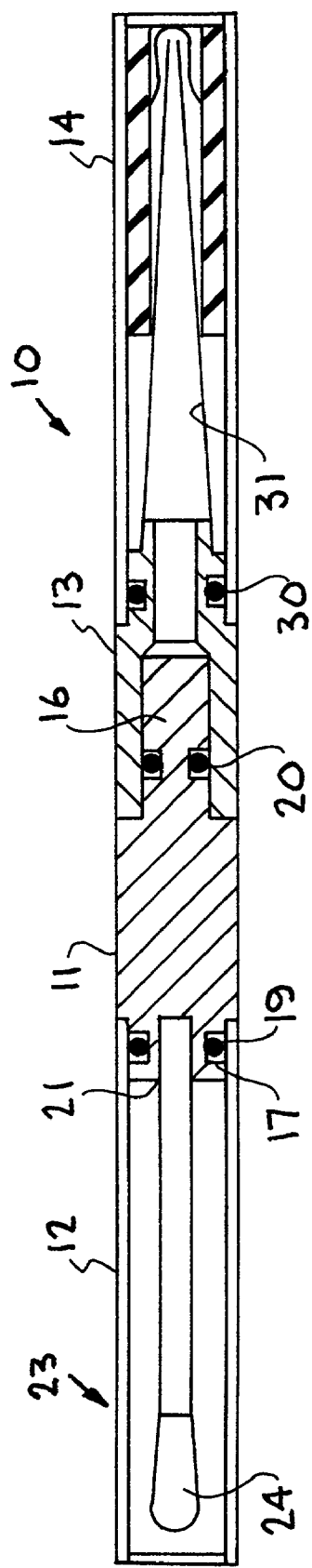
FIG. 2 is a partial cross-sectional view of the sampler of FIG. 1.
Figure 3:
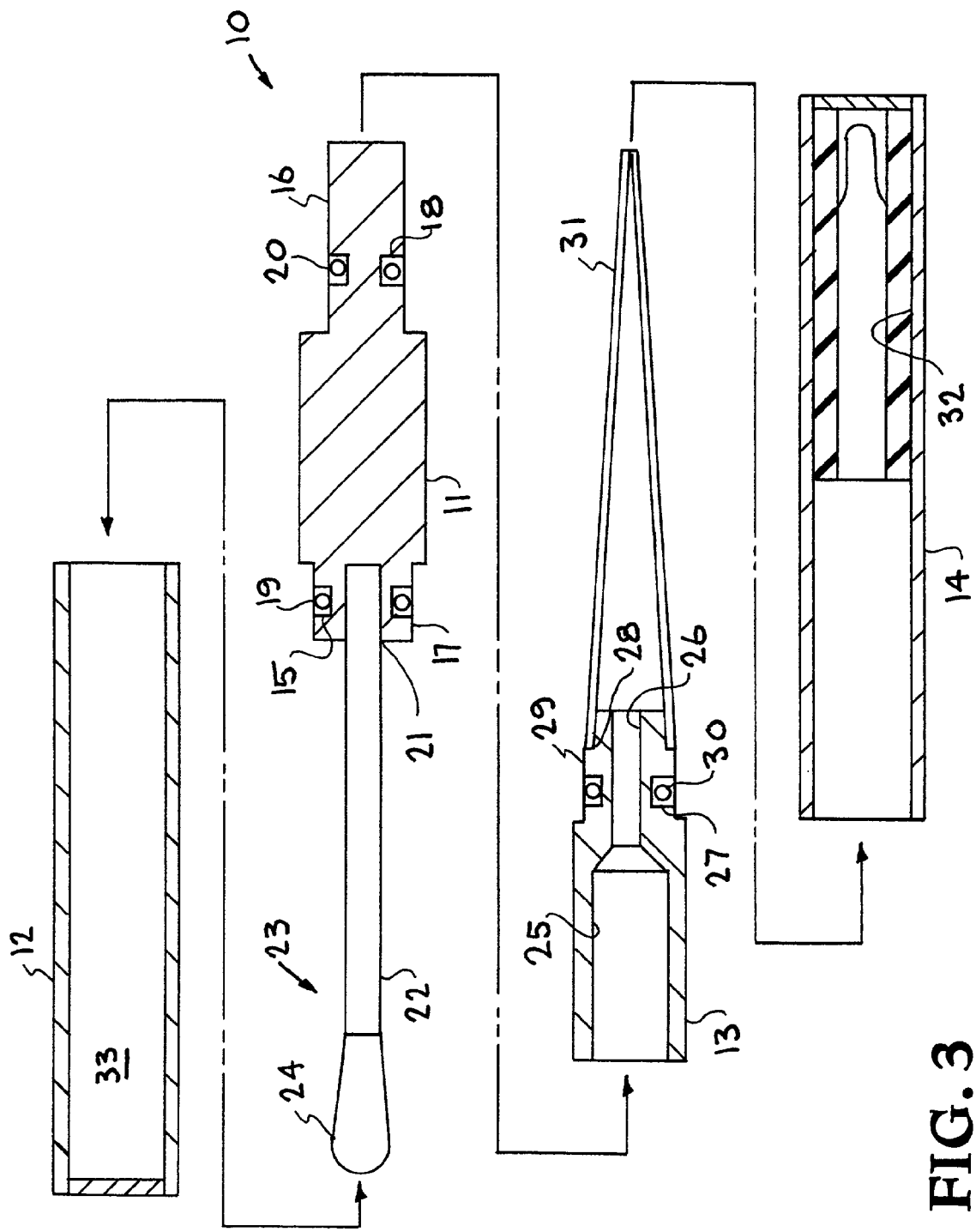
FIG. 3 is an exploded partial cross-sectional view of the FIG. 2 sampler.

Referring now to the drawings, FIG. 1 is an external view of an embodiment of the residue sampler applicator made in accordance with the present invention, with FIG. 2 being a cross-sectional view of the sampling apparatus of FIG. 1, and FIG. 3 being an exploded view in cross-section of the FIG. 2 apparatus.

As shown in FIG. 1, the sampler applicator or sampling apparatus, generally indicated at 10, is composed of a first body or barrel section 11 to which an end cap or tube 12 is hermetically mounted, and to which a second body or barrel section 13 is hermetically mounted, with an end cap or tube 14 hermetically mounted to said second body or barrel section 13. The apparatus 10 of FIG. 1 is shown in its actual size with a length as indicated by arrow a of 5.938 inches, and a width or cross-section as indicated by arrow b of ⅜ inches. For example, the components 11, 12, 13 and 14 may be composed of stainless steel or titanium.

As seen in FIGS. 2 and 3, the first body or barrel section 11 includes reduced diameter end sections 15 and 16 having therein grooves 17 and 18 in which are located σ-ring seals 19 and 20. Reduced diameter end section 15 is provided with a cavity 21 in which one end of a member or handle 22 of a sponge assembly 23 having a sponge 24 mounted to the opposite end of handle 22, is removably mounted. End cap 12 forms a hollow tube, which as pointed out above would, in use, contain a known amount of a selected solvent, such as acetone, methylene, or chloride by which sponge 24 is wetted. Sponge 24 may be composed of cotton or foam with handle 22 constructed of plastic. σ-ring seals 19 functions to hermetically seal and retain end cap 12 over the reduced diameter end section 15 of barrel section 11. The end cap 12 can be removed from the barrel section 11 by pulling so as to expose the wetted sponge 24 to an analyte of interest as described above, and thereof hermetically resealed by movement over the σ-ring 19.

The second body or barrel section 13, as seen in FIGS. 2 & 3, comprises a housing having a central aperature therein of different diameter sections 25 and 26 and includes a pair of reduced end diameter sections 27 and 28 of different diameters. Reduced end section 27 being provided with a groove 29 in which an σ-ring seal 30 is located, and a pipette tip 31 is removably mounted by friction fit, for example, to reduced diameter end section 28. Located in end cap 14 is a vial 32 in which dissolved sample squeezed from sponge 24 through pipette tip 31 is collected, as described above. As shown in FIG. 2, second barrel section 13 is hermetically mounted on reduced end section 16 and sealed to the first barrel section 11 via σ-ring seal 20, and end cap 14 is hermetically mounted on reduced end section 27 and sealed to the second barrel section 13 via σ-ring 30, with pipette tip 31 extending into vial 32 during storage or transport. As seen in FIG. 3, end cap 12 which in actual use contains a known quantity of a known solvent indicated at 33 is removed from first barrel section 11, as indicated by arrow c, the second barrel section 13 with pipette tip 31 is removed from the first barrel section 11, as indicated by arrow d, and end cap 14 with vial 32 is removed from the second barrel section 13, as indicated by arrow e, for use of the sponge 24, pipette tip 31, and vial 32 as described above. Following the sample collection and transfer to an analysis system, the components may be recombined as shown in FIG. 2.

It has thus been shown that the present invention provides a small, robust sampling apparatus, with sample dissolution, and sample applicator features. The components of the apparatus are hermetically sealing thereby preventing cross-contamination or leakage from the apparatus. Since the apparatus is hermetically sealed, it may be submitted to decontamination solutions before it is handled or shipped. Thus, this invention enable field-deployment of the sample apparatus, which can be used in conjunction with thin layer chromatography or other analysis systems.

While a specific embodiment, along with materials, parameters, etc. have been described and/or illustrated, such is not intended to be limiting. Modifications and changes may become apparent to those skilled in the art, and it is intended that the invention be limited only by the scope of the appended claims.

What is claimed is:

1. A device for collecting residue, comprising:
   a first barrel section,
   a sponge removably mounted to said first barrel section,
   a first end cap removably mounted to said first barrel section,
   a second barrel section having a sponge insertable opening extending therethough, said second barrel section removably mounted to the first barrel section so that the opening is occluded thereby,
   a pipette tip removably mounted to said second barrel section and in fluidic communication with the opening, and
   a second end cap removably mounted to said second barrel section.

2. The device of claim 1, additionally including a vial mounted in said second end cap.

3. The device of claim 1, wherein said first barrel section includes a reduced diameter section at opposite ends thereof, said first end cap and said second barrel section being removably mounted to said reduced diameter sections.

4. The device of claim 3, additionally including seal means mounted on each said reduced diameter section of said first barrel section.

5. The device of claim 4, wherein each said seal means includes a groove in said reduced diameter section and an σ-ring located in said groove.

6. The device of claim 1, additionally including seal means located intermediate said first end cap and said first barrel section, intermediate said first barrel section and said second barrel section, and intermediate said second barrel section and said section end cap.

7. The device of claim 1, wherein said sponge is mounted to said first barrel section via a member removably mounted in a cavity in said first barrel section.

8. The device of claim 1, wherein said second barrel section includes two reduced diameter sections of which one section is smaller in diameter than the other section, said second end cap being removably mounted to said one section, and said pipette tip being removably mounted to said other section.

9. The device of claim 8, wherein said one section of said two reduced diameter sections is provided with a seal means.

10. The device of claim 8, wherein said seal means comprise a groove in said one section and an σ-ring mounted in said groove.

11. The device of claim 1, wherein said first end cap is hermetically sealed to said first barrel section, said second barrel section is hermetically sealed to said first barrel section, and said second end cap is hermetically sealed to said second barrel section.

12. The device of claim 11, additionally including a vial mounted in said second end cap.

13. The device of claim 12, additionally including a quantity of solvent in said first end cap.

14. The device of claim 1, wherein said opening has a reduced diameter section for inhibiting passage of the sponge when inserted into the opening towards the pipette tip.

* * * * *